United States Patent
Watanabe et al.

(10) Patent No.: US 9,250,138 B2
(45) Date of Patent: Feb. 2, 2016

(54) TEMPERATURE DETECTING DEVICE AND METHOD

(71) Applicant: DENSO CORPORATION, Kariya, Aichi-pref. (JP)

(72) Inventors: Kazunori Watanabe, Kariya (JP); Tsuneo Maebara, Nagoya (JP); Junichi Fukuta, Kuwana (JP)

(73) Assignee: DENSO CORPORATION, Kariya (JP)

( * ) Notice: Subject to any disclaimer, the term of this patent is extended or adjusted under 35 U.S.C. 154(b) by 372 days.

(21) Appl. No.: 13/894,880

(22) Filed: May 15, 2013

(65) Prior Publication Data

US 2013/0322487 A1    Dec. 5, 2013

(30) Foreign Application Priority Data

Jun. 1, 2012   (JP) .................. 2012-125670

(51) Int. Cl.
*G01K 7/02* (2006.01)
*G01N 25/72* (2006.01)
*G01K 1/02* (2006.01)
*G01K 7/01* (2006.01)
(Continued)

(52) U.S. Cl.
CPC *G01K 7/02* (2013.01); *G01K 1/026* (2013.01); *G01K 7/01* (2013.01); *G01N 25/72* (2013.01)

(58) Field of Classification Search
CPC .......... G01K 7/02; G01K 7/021; G01K 7/01; G01K 1/026; G01N 25/72; G01N 29/449
USPC ..................... 374/4, 183, 178, 163
See application file for complete search history.

(56) References Cited

U.S. PATENT DOCUMENTS

| | | | |
|---|---|---|---|
| 4,636,092 A * | 1/1987 | Hegyi | 374/178 |
| 2009/0046761 A1* | 2/2009 | Pan | 374/178 |
| 2010/0188135 A1* | 7/2010 | Keronen et al. | 327/482 |

FOREIGN PATENT DOCUMENTS

| | | |
|---|---|---|
| JP | 10-38964 | 2/1998 |
| JP | 2003-294540 | 10/2003 |
| JP | 2008-164469 | 7/2008 |

(Continued)

OTHER PUBLICATIONS

English Machine Translation of JP 2009071914 A, Ogawa, Apr. 2, 2009.*

(Continued)

*Primary Examiner* — Lisa Caputo
*Assistant Examiner* — Philip Cotey
(74) *Attorney, Agent, or Firm* — Nixon & Vanderhye PC

(57) ABSTRACT

A temperature detecting device for a power conversion device is provided in which the number of components can be reduced. An exemplary embodiment of the temperature detecting device includes: a plurality of temperature detecting elements that are provided in correspondence with a plurality of temperature detection objects, each temperature detecting element outputting a signal having a correlation with the temperature of the temperature detection object by being supplied power by a common power source; and a temperature detector that detects the temperatures of the temperature detection objects based on the signals having correlation with the temperatures of the temperature detection objects outputted from the temperature detecting elements. The temperature detector detects an average temperature of at least two temperature detection objects among the plurality of temperature detection objects or respective temperatures of the plurality of temperature detection objects based on the output signals.

19 Claims, 8 Drawing Sheets

(56) References Cited

FOREIGN PATENT DOCUMENTS

| | | | |
|---|---|---|---|
| JP | 2009071914 A | * | 4/2009 |
| JP | 2009-171312 | | 7/2009 |

OTHER PUBLICATIONS

Official Action (1 page) dated Mar. 11, 2014, issued in corresponding Japanese Application No. 2012-125670 and English translation (1 page).

* cited by examiner

FIG.7  THIRD EMBODIMENT

FOURTH EMBODIMENT

TEMPERATURE DETECTING DEVICE AND METHOD

CROSS-REFERENCE TO RELATED APPLICATION

This application is based on and claims the benefit of priorities from earlier Japanese Patent Application No. 2012-125670 filed Jun. 1, 2012, the description of which is incorporated herein by reference.

BACKGROUND OF THE INVENTION

1. Field of the Invention

The present invention relates to a temperature detecting device that detects the temperature of a temperature detection object based on an output signal from a temperature detecting element. The temperature detecting device is used, for example, to detect the temperature of a switching element in a power conversion device (inverter or converter) of a motor generator.

2. Description of the Related Art

For example, as shown in JP-A-2009-171312, a temperature detecting device is conventionally known that detects the temperature of an inverter by a thermo-sensitive diode. In this device, one end of the two ends of the thermo-sensitive diode is connected to a constant current power source. The other end is grounded. The temperature of the inverter is detected based on a potential difference between the two ends of the thermo-sensitive diode.

Here, when a plurality of temperature detection areas are present within the inverter, the number of thermo-sensitive diodes required adheres to the number of temperature detection areas. Should a constant current power source be provided in correspondence with each of the plurality of thermo-sensitive diodes, the number of components configuring the temperature detecting device increases. As a result, the configuration of the temperature detecting device becomes complex, and cost increases.

Therefore, a new temperature detecting device is desired in which the number of components configuring the temperature detecting device can be reduced.

SUMMARY

As an exemplary embodiment, the present application provides a temperature detecting device comprising: a plurality of temperature detecting elements that are provided in correspondence with a plurality of temperature detection objects, and each temperature detecting element outputting a signal having a correlation with the temperature of the temperature detection object by being supplied power; and a temperature detector that detects the temperatures of the plurality of temperature detection objects based on the output signals from the plurality of temperature detecting elements. The plurality of temperature detecting elements are connected in series or in parallel. The plurality of temperature detecting elements are each supplied power by a common power source. The temperature detector detects an average temperature of at least two temperature detection objects among the plurality of temperature detection objects, or respective temperatures of the plurality of temperature detection objects based on the output signals.

In the temperature detecting device of the present application, the plurality of temperature detecting elements and the temperature detector are configured according to the above-described aspect. The average temperature is detected to simplify the temperature detection device. Alternatively, the respective temperatures of the plurality of temperature detection objects are detected to enhance detection accuracy of the temperatures of the temperature detection objects.

In addition, in the above-described exemplary embodiment, the plurality of temperature detecting elements are each supplied power by a common power source. Therefore, for example, compared to a configuration in which power sources are provided in correspondence with the plurality of temperature detecting elements, the number of components, such as power sources, configuring the temperature detecting device can be effectively reduced.

Furthermore, because the common power source is provided, for example, compared to a configuration in which power sources are provided in correspondence with the plurality of temperature detecting elements, reduction in temperature detection accuracy caused by lo variations in output power of the power sources attributed to individual differences among the power sources can also be prevented.

DETAILED DESCRIPTION OF THE PREFERRED EMBODIMENTS (First Embodiment)

A first embodiment will be described with reference to the drawings. According to the first embodiment, a temperature detecting device of the present invention is applied to a hybrid car including a rotating electrical machine as a main car-driving engine and an internal combustion engine as a supplemental car-driving engine.

Figure 1:
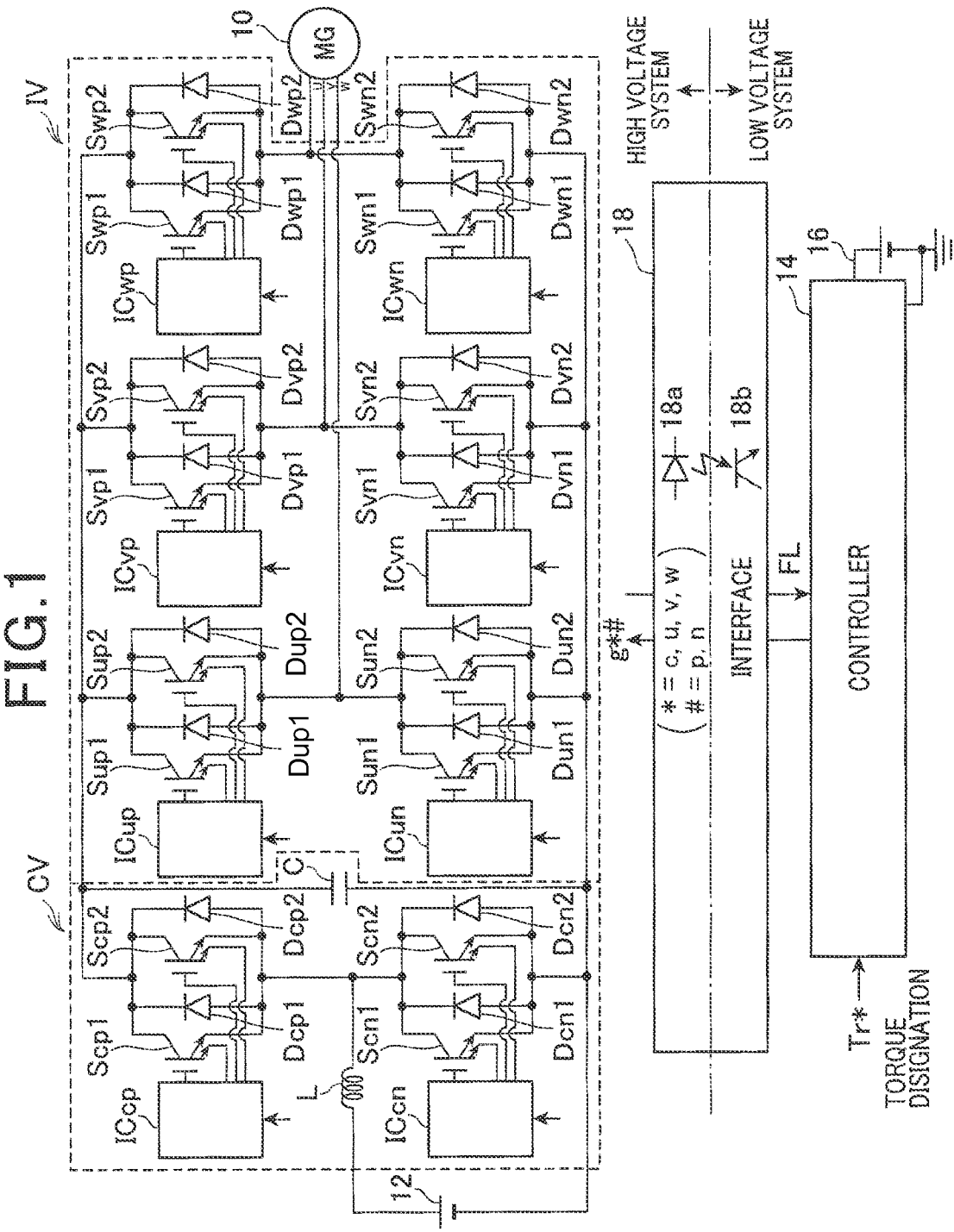
FIG. 1 is an overall configuration diagram of a system according to a first embodiment.

FIG. 1 shows an overall configuration of a system according to the first embodiment.

A motor generator 10 serving as the main car-driving engine is connected to a driving wheel (not shown). The motor generator 10 is connected to a high voltage battery 12 with an inverter IV and a converter CV therebetween.

The converter CV includes a capacitor C, a parallel-connected member composed of a pair of switching elements Scp1 and Scp2, a parallel-connected member composed of a pair of switching elements Scn1 and Scn2, and a reactor L. Specifically, a member (serially connected member) configured by the parallel-connected member composed of the switching elements Scp1 and Scp2 and the parallel-connected member composed of the switching elements Scn1 and Scn2 being connected in series is connected in parallel with the capacitor C. The connection point of the serially connected member and the positive terminal of the high voltage battery 12 are connected by the reactor L. The converter CV provides a function for increasing the voltage (such as 288 volts) of the high voltage battery 12, to a predetermined voltage (such as 666 volts) set as an upper limit, by ON/OFF operation of the switching elements Scp1, Scp2, Scn1, and Scn2.

On the other hand, the inverter IV includes a member (serially connected member) configured by a parallel-connected member composed of a pair of switching elements Sup1 and Sup2 and a parallel-connected member composed of a pair of switching elements Sun1 and Sun2 being connected in series, a member (serially connected member) configured by a parallel-connected member composed of a pair of switching elements Svp1 and Svp2 and a parallel-connected member composed of a pair of switching elements Svn1 and Svn2 being connected in series, and a member (serially connected member) configured by a parallel-connected member composed of a pair of switching elements Swp1 and Swp2 and a parallel-connected member composed of a pair of switching elements to Swn1 and Swn2 being connected in series. The respective connection points of the serially connected members are respectively connected to the U-phase, V-phase, and W-phase of the motor generator 10.

According to the first embodiment, voltage control type switching elements are used as the switching elements $S*\#¥$ ($*$=c,u,v,w; $\#$=p,n; $¥$=1,2). Specifically, insulated-gate bipolar transistors (IGBT) are used. In addition, a freewheeling diode $D*\#¥$ is connected in reverse parallel to each of the switching elements $S*\#¥$. Furthermore, a thermo-sensitive diode (not shown) that detects the temperature of the switching element $S*\#¥$ is provided near the switching element $S*\#¥$. The thermo-sensitive diode will be described hereafter.

According to the first embodiment, the switching elements $S*\#¥$ configuring the converter CV and the inverter IV are structured as parallel-connected members, each composed of a pair of switching elements. A reason for this is to increase the maximum values of the output currents of the converter CV and the inverter IV.

A controller (referred to, hereinafter, as a "control circuit") 14 uses a low voltage battery 16 as a power source. The control circuit 14 operates the inverter IV and the converter CV to control the torque of the motor generator 10 to a torque designated value Tr*. Specifically, the control circuit 14 operates the switching elements Scp¥ and Scn¥ of the converter CV by outputting operating signals gcp and gcn to drive circuits ICcp and ICcn. In addition, the control circuit 14 operates the switching elements Sup¥, Sun¥, Svp¥, Svn¥, Swp¥, and Swn¥ of the inverter IV by outputting operating signals gup, gun, gyp, gvn, gwp, and gwn to drive circuits ICup, ICun, ICvp, ICvn, ICwp, and ICwn. Here, the operating signal g*p of the high potential side and the corresponding operating signal g*n of the low potential side are complementary signals. In other words, the switching element S*p¥ on the high potential side and the corresponding switching element S*n¥ on the low potential side are alternately turned ON. Therefore, the direct-current voltage of the high voltage battery 12 can be converted to an alternating-current voltage, and the motor generator 10 can be driven (during power-running operation). In addition, the alternating-current voltage occurring in the motor generator 10 can be converted to a direct-current voltage, and the high voltage battery 12 can be charged (during regeneration operation).

The pair of switching elements $S*\#1$ and $S*\#2$ can be turned ON and OFF by a common operating signal $g*\#$ because the emitters of the switching elements $S*\#1$ and $S*\#2$ are short-circuited. In addition, the torque designated value Tr* is, for example, inputted from an higher-order control device that oversees control of the vehicle.

Within the system, an interface 18 is a device for receiving and transmitting signals between a "high voltage system" including the high voltage battery 12 and a "low voltage system" including the low voltage battery 16, while electrically insulating the high voltage system and the low voltage system. According to the first embodiment, a photo-coupler is used as the interface 18. According to the first embodiment, the high voltage system is equivalent to a "first region" and the low voltage system is equivalent to a "second region".

Figure 2:
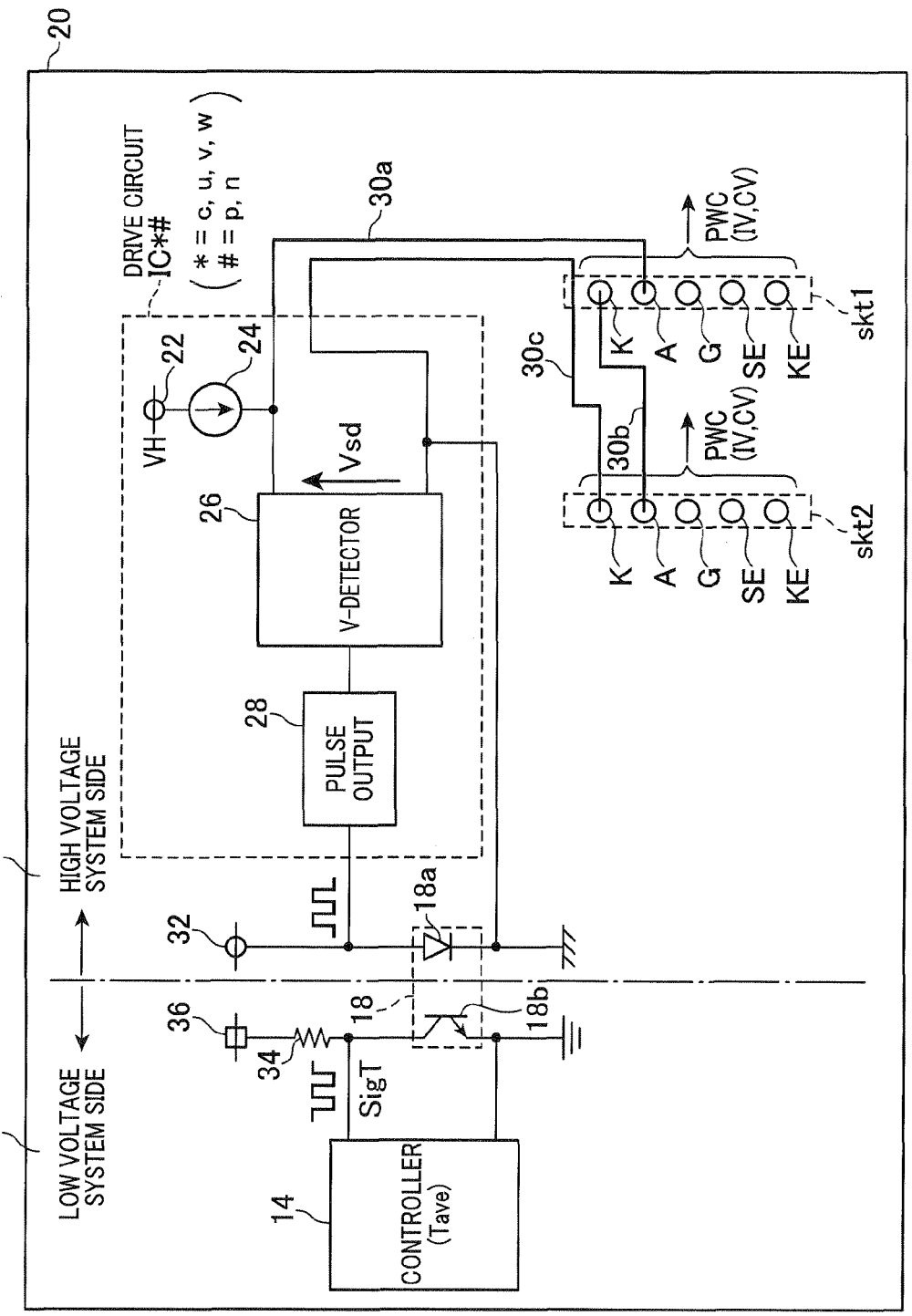
FIG. 2 is a diagram of a component layout on a PCB according to the first embodiment.

Next, a printed circuit board on which semiconductor chips are mounted (referred to, hereinafter, as "PCB") 20 that is connected to the inverter IV and the converter CV will be described with reference to FIG. 2. FIG. 2 is a diagram of a component layout on the surface of the PCB 20. As shown in FIG. 2, the surface of the PCB 20 is rectangular. The control circuit 14 and the drive circuits IC*# are mounted on the PCB 20. In addition, a pair of attaching sections (referred to, hereinafter, as a first attaching section skt1 and a second attaching section skt2) are provided on the PCB 20. The first attaching section skt1 and the second attaching section skt2 electrically connect power cards PWC on the underside of the PCB 20. In FIG. 2, the layout of components for detecting the temperature of a certain pair of switching elements $S*\#1$ and $S*\#2$, among the switching elements $S*\#¥$ included in the inverter IV and the converter CV, is shown. However, the components for turning ON and OFF the switching elements $S*\#1$ and $S*\#2$ and the thermo-sensitive diodes $T*\#¥$ described hereafter are omitted. According to the first embodiment, the switching element $S*\#1$ is referred to, hereinafter, as a "first switching element" and the switching element $S*\#2$ is referred to as a "second switching element".

As shown in FIG. 2, the region of the PCB 20 including the control circuit 14 is the low voltage system. The remaining region configures a portion of the high voltage system.

Figure 3:
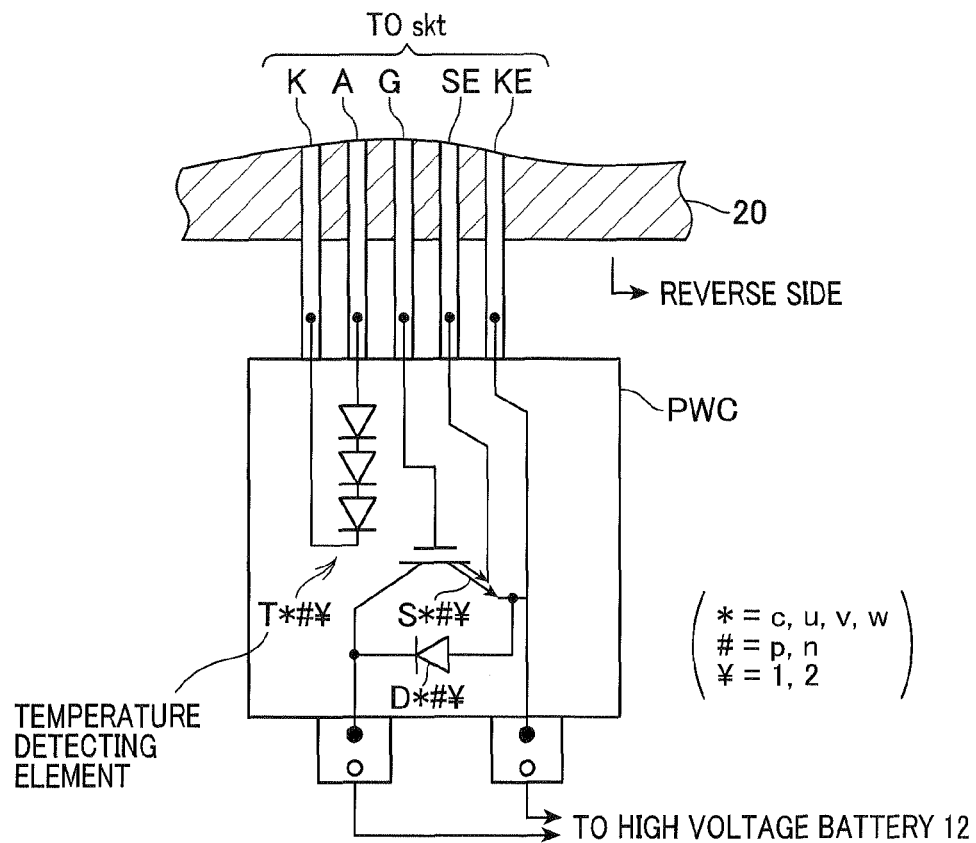
FIG. 3 is a diagram of a power card according to the first embodiment.

FIG. 3 shows a state in which a power card PWC is electrically connected on the underside of the PCB 20. The switching element $S*\#¥$ is packaged by being housed in the power card PWC together with the freewheeling diode $D*\#¥$ and the thermo-sensitive diode $T*\#¥$. One thermo-sensitive diode detects the temperature of a single switching element. In other words, at least one thermo-sensitive diode is provided within the power card in correspondence with each switching element that is a temperature detection object. As shown in FIG. 3, the first switching element $S*\#1$ and the second switching element $S*\#2$ are connected to the PCB 20 by being inserted from the back surface (the underside of the surface shown in FIG. 2) side of the PCB 20. In FIG. 3, a plurality of thermo-sensitive diodes (three thermo-sensitive diodes) are connected in series as the thermo-sensitive diode $T*\#¥$. However, this is not limited thereto. The thermo-sensitive diode $T*\#¥$ may be a single thermo-sensitive diode. In addition, according to the first embodiment, hereinafter, the thermo-sensitive diode $T*\#1$ corresponding with the first switching element $S*\#1$ is referred to as a "first thermo-sensitive diode", and the thermo-sensitive diode $T*\#2$ corresponding with the second switching element $S*\#2$ is referred to as a "second thermo-sensitive diode".

The power card PWC is configured such that an open/close control terminal (gate G), a Kelvin emitter electrode KE, a sense terminal SE, and an anode A and a cathode K of the thermo-sensitive diode $T*\#¥$ are each inserted into terminal insertion holes of the attaching sections skt1 and skt2 of the above-described PCB 20 from the underside of the PCB 20. The power card PWC is thereby electrically connected to the drive circuit IC*#. Here, the Kelvin emitter electrode KE is an electrode having the same electric potential as the emitter of the switching element S*#¥. The sense terminal SE is a terminal for outputting a minute current having a correlation with the current flowing through the switching element S*#¥.

Returning to the description with reference to FIG. 2, the high voltage system includes the pair of attaching sections (the first attaching section skt1 and the second attaching section skt2) corresponding with the pair of power cards PWC, and the drive circuit IC*#. According to the first embodiment, through holes are formed in each of the first attaching section skt1 and second attaching section skt2 to attach the cathode K, the anode A, the gate G, the sense terminal SE, and the Kelvin emitter electrode KE sequentially in a linear array. The first attaching section skt1 and the second attaching section skt2 are rectangular and provided adjacent to each other such that the respective long sides are parallel with each other. As shown in FIG. 3, the power card PWC includes two terminals for connecting to the positive electrode and the negative electrode of the high voltage battery 12 (see FIG. 1).

Next, the drive circuit will be described with reference to FIG. 2. The drive circuit IC*# is a semiconductor integrated circuit formed into a single chip. The drive circuit IC*# is the area surrounded by the dotted line in FIG. 2. The drive circuit includes a constant voltage power source 22 having a terminal voltage VH, a constant current power source 24, a voltage detection circuit 26 serving as a temperature detector, and a pulse signal output circuit 28.

The constant current power source 24 uses the constant voltage power source 22 as a power supply source. The output side of the constant current power source 24 is connected to the voltage detection circuit 26, and to the anode A of the first attaching section skt1 via a wiring pattern 30a formed on the PCB 20. The cathode K of the first attaching section skt1 is connected to the anode A of the second attaching section skt2 via a wiring pattern 30b. The cathode K of the second attaching section skt2 is connected to the voltage detection circuit 26, and to the ground portion on the high voltage system side via a wiring pattern 30c. The configuration is used to detect a potential difference Vsd between both ends of a serially connected member composed of the first thermo-sensitive diode T*#1 included within one power card PWC and the second thermo-sensitive diode T*#2 included within the other power card PWC. The wiring pattern 30c has portions parallel with the wiring pattern 30a, and portions parallel with the wiring pattern 30b.

Figure 4:
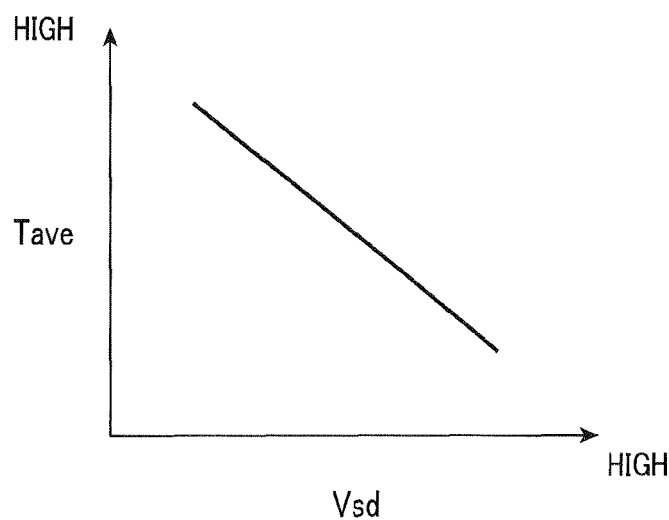
FIG. 4 is a diagram of a relationship between a voltage detection value and an average temperature of a pair of switching elements.

Next, a relationship between the voltage detection value and the average temperature of a pair of switching elements will be described with reference to FIG. 4. The voltage detection circuit 26 detects the potential difference Vsd between both ends of the serially connected member composed of the first thermo-sensitive diode T*#1 and the second thermo-sensitive diode T*#2, via the wiring pattern 30a and the wiring pattern 30c. The wiring pattern 30a and the wiring pattern 30c serve as wiring patterns for output signal detection. In other words, the voltage detection circuit 26 detects the potential on the output side of the constant current power source 24 in relation to ground potential. The potential difference Vsd is a sum of the respective voltage drop amounts of the first thermo-sensitive diode T*#1 and the second thermo-sensitive diode T*#2. As a result, the sum of the temperature of the first switching element S*#1 and the temperature of the second switching element S*#2, described hereafter, is determined. A value obtained by the added value of the temperatures of the first switching element S*#1 and the second switching element S*#2 being divided by "2" is an average temperature Tave of the first switching element S*#1 and the second switching element S*#2. The potential difference Vsd and the average temperature Tave have a negative correlation as shown in FIG. 4.

The potential difference Vsd detected by the voltage detection circuit 26 is outputted to the pulse signal output circuit 28. The pulse signal output circuit 28 outputs a signal correlated with the potential difference Vsd. According to the first embodiment, the pulse signal output circuit 28 outputs a time ratio signal adhering to the potential difference Vsd as a signal having the correlation. Here, specifically, the smaller the potential difference Vsd is, the smaller the time ratio of the time ratio signal outputted.

The output side of the pulse signal output circuit 28 is connected to a connection point of a constant voltage power source 32 and a primary side (photodiode 18a) of a photo-coupler serving as the interface 18. Of the two ends of the photodiode 18a, the side opposite to the constant voltage power source 32 is connected to a ground portion.

On the other hand, the collector on a secondary side (phototransistor 18b) of the photo-coupler is connected to a constant voltage power source 36 with a resistor 34 therebetween. The emitter is connected to a ground portion on the low voltage system side. According to the first embodiment, the potential at the connection point of the resistor 34 and the phototransistor 18b is referred to as a temperature detection signal SigT.

According to the configuration such as this, when the logic of the output signal of the pulse signal output circuit 28 is "Low", the current flowing from the constant voltage power source 32 to the photodiode 18a decreases. The photodiode 18a is thereby set to the OFF state. Therefore, the phototransistor 18b is set to the OFF state, and the potential at the connection point of the resistor 34 and the phototransistor 18b increases. As a result, the logic of the temperature detection signal SigT becomes "High". On the other hand, when the logic of the output signal of the pulse signal output circuit 28 is "High", the photodiode 18a is set to the ON state. Therefore, the phototransistor 18b switches to the ON state, and the potential at the connection point between the resistor 34 and the phototransistor 18b decreases to the ground potential. As a result, the logic of the temperature detection signal SigT becomes "Low".

The control circuit 14 calculates the average temperature Tave based on the temperature detection signal SigT. The average temperature Tave can be determined by a table (such as the relationship between the potential difference Vsd and the average temperature Tave in FIG. 4) in which the relationship is measured in advance and stored in a non-volatile manner. When judged that the average temperature Tave exceeds a threshold temperature, the control circuit 14 performs a power save process to reduce the torque designated value Tr*. As a result of the power save process, the driving of the switching element S*#¥ is restricted and the collector current is restricted. As a result, overheating of the switching element S*#¥ can be prevented.

The configuration for transmitting information related to the average temperature Tave to the control circuit 14 via the interface 18 can, in actuality, be provided in correspondence with only a single pair among the plurality of pairs of switching elements S*#1 and S*#2 included in the converter CV and the inverter IV. Specifically, the configuration is provided in correspondence with the pair, among the plurality of pairs, in which the temperature of the switching elements is expected to become the highest. As a result, compared to a configuration in which the photo-coupler and the like are provided for each of the plurality of pairs, the number of components such as the photo-coupler can be reduced. The temperature of each switching element S*#¥ included in the converter CV and the inverter IV differs as a result of the effects cooling paths for a coolant for cooling the switching elements S*#¥ and the layout positions of the switching elements S*#¥ have on the temperatures of the switching elements S*#¥.

The method of connecting the constant current power source 24, the first thermo-sensitive diode T*#1, and the second thermo-sensitive diode T*#2 via the wiring patterns 30a to 30c and the method of laying out the wiring patterns 30a to 30c on the PCB 20 are characteristic configurations according to the first embodiment. These characteristics will hereinafter be described in comparison with a first idea (not prior art) of the inventors of the present invention.

Figure 5:
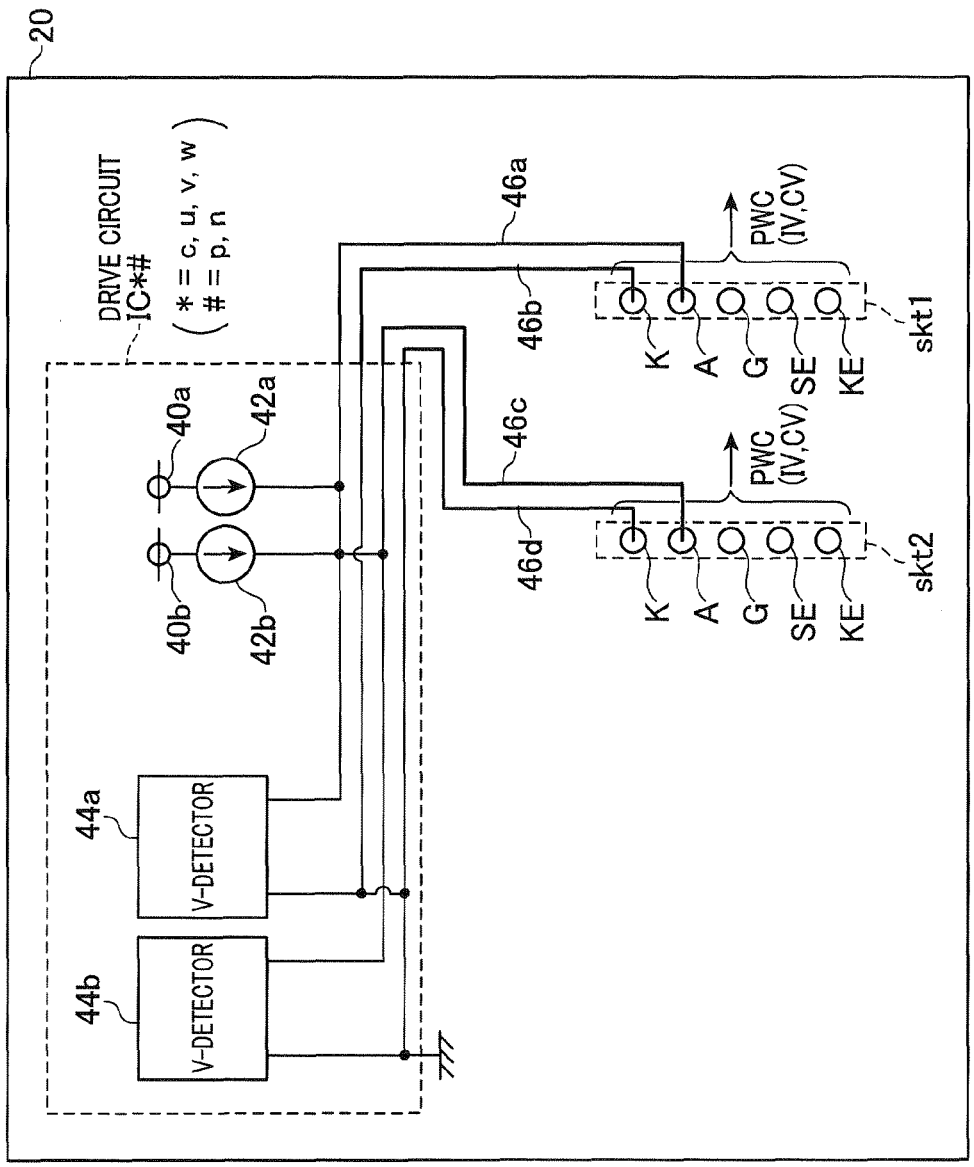
FIG. 5 is a planar view of a PCB according to first idea of the inventors (not prior art)

First, FIG. 5 shows a planar view of the PCB 20 according to the first idea of inventors. Components and the like in FIG. 5 that are the same as those in FIG. 2 are given the same reference numbers for convenience. The pulse signal output circuit 28 and the low potential system side shown in FIG. 2 are omitted in FIG. 5.

As shown in FIG. 5, the drive circuit IC*# on the PCB 20 includes a pair of constant voltage power sources 40a and 40b, a pair of constant current power sources 42a and 42b, and a pair of voltage detection circuits 44a and 44b. The constant current power source 42a uses the constant voltage power source 40a as the power supply source. The output side of the constant current power source 42a is connected to the voltage detection circuit 44a and to the anode A of the first attaching section skt1 via a wiring pattern 46a. The cathode K of the first attaching section skt1 is connected to the voltage detection circuit 44a and to the ground portion on the high voltage system side via a wiring pattern 46b. The wiring patterns 46a and 46b are formed such as to be parallel with each other from a front view of the surface of the PCB 20.

On the other hand, the constant current power source 42b uses the constant voltage power source 40b as the power supply source. The output side of the constant current power source 42a is connected to the voltage detection circuit 44b and to the anode A of the second attaching section skt2 via a wiring pattern 46c. The cathode K of the second attaching section skt2 is connected to the voltage detection circuit 44b and to the ground portion via a wiring pattern 46d. The wiring patterns 46c and 46d are formed such as to be parallel with each other on the PCB 20.

The voltage detection circuit 44a detects the potential difference between both ends of the first thermo-sensitive diode T*#1. The voltage detection circuit 44b detects the potential difference between both ends of the second thermo-sensitive diode T*#2.

Next, the characteristic configurations according to the first embodiment will be described.

As shown in above-described FIG. 2, according to the first embodiment, a single closed loop circuit including the single constant current power source 24 and the thermo-sensitive diodes T*#1 and T*#2 is formed. As a result, the number of components, such as the constant current power source and the voltage detection circuit, can be reduced. The circuit configuration can be simplified. In addition, the cost of the control system of the motor generator 10 can be reduced.

On the other hand, in the first idea of the inventors shown in FIG. 5, the constant current power sources 42a and 42b, the voltage detection circuits 44a and 44b, and the like corresponding to each of the thermo-sensitive diodes T*#1 and T*#2 are included. Therefore, the circuit configuration becomes complex. The cost of the control system of the motor generator 10 increases.

In addition, as shown in above-described FIG. 2, according to the first embodiment, the wiring patterns 30a and 30b, and the wiring pattern 30c are formed on the PCB 20 such as to be parallel with each other. In particular, according to the first embodiment, the wiring patterns 30a to 30c are formed such as to be concentrated in one area of the PCB 20. Therefore, for example, even when noise interference occurs from the patterns 30a and 30c, the noise becomes common mode noise that is transmitted from both ends of the serially connected member composed of the first thermo-sensitive diode T*#1 and the second thermo-sensitive diode T*#2 towards the voltage detection circuit 26. Therefore, the effect noise interference has on the detection accuracy of the average temperature Tave, based on the potential difference Vsd, can be reduced.

On the other hand, in the first idea of the inventors shown in FIG. 5, there is an area in which the degree of separation of the set of wiring patterns 46a and 46b, corresponding to the first attaching section skt1, from the wiring patterns 46c and 46d, corresponding to the second attaching section skt2, is large. Therefore, the detection accuracy of the temperatures of the switching elements may decrease. Specifically, for example, when noise interference occurs only from the wiring patterns 46a and 46b, the noise is transmitted from the wiring pattern 46b side connected to the ground portion towards the wiring 46d side. The accuracy of detection of the temperature of the second switching element S*#2 via the wiring patterns 46c and 46d may decrease.

(Effects According to the First Embodiment)

The following effects can be achieved according to the first embodiment, described in detail above.

(1) The first thermo-sensitive diode T*#1 and the second thermo-sensitive diode T*#2 are connected in series. A current is supplied to the serially connected member composed of the thermo-sensitive diodes T*#1 and T*#2 from the constant current power source 24. As a result of the potential difference between both ends of the serially connected member being detected by the voltage detection circuit 26, the average temperature Tave of the first switching element S*#1 and the second switching element S*#2 is detected. Therefore, for example, compared to a configuration in which a constant current power source and the like are provided in correspondence with each thermo-sensitive diode T*#1 and T*#2, the number of components for detecting the temperature of the switching element can be reduced.

The average temperature Tave is detected and transmitted to the control circuit 14. Therefore, for example, compared to a configuration in which the respective temperatures of the first switching element S*#1 and the second switching element S*#2 are transmitted to the control circuit 14 by photo-couplers respectively corresponding to the switching elements S*#1 and S*#2, the number of components, such as the photo-coupler, can be reduced. As a result of the configuration such as this, the cost of the control system of the motor generator 10 can be favorably reduced.

Furthermore, a current is supplied to each of the first thermo-sensitive diode T*#1 and the second thermo-sensitive diode T*#2 by a common constant current power source 24. Therefore, for example, compared to a configuration in which a constant current power source is provided in correspondence with each thermo-sensitive diode T*#¥, reduction in detection accuracy of the temperature of the switching element caused by variations in output currents of the constant current power sources attributed to individual differences among the constant current power sources can be prevented.

(2) The wiring patterns 30a and 30b, and the wiring pattern 30c are formed on the surface of the PCB 20 such as to be parallel with each other. In addition, the wiring patterns 30a to 30c are formed such as to be concentrated in one area of the PCB 20. Therefore, noise resistance related to the detection of the average temperature Tave can be enhanced.

(Second Embodiment)

A second embodiment will hereinafter be described with reference to the drawings, mainly focusing on the differences with the first embodiment.

According to the second embodiment, in place of the configuration in which the average temperature Tave of the switching element S*#1 and the second switching element S*#2 is detected, a configuration is used in which respective temperatures T1 and T2 of the switching elements S*#1 and S*#2 are detected.

Figure 6:
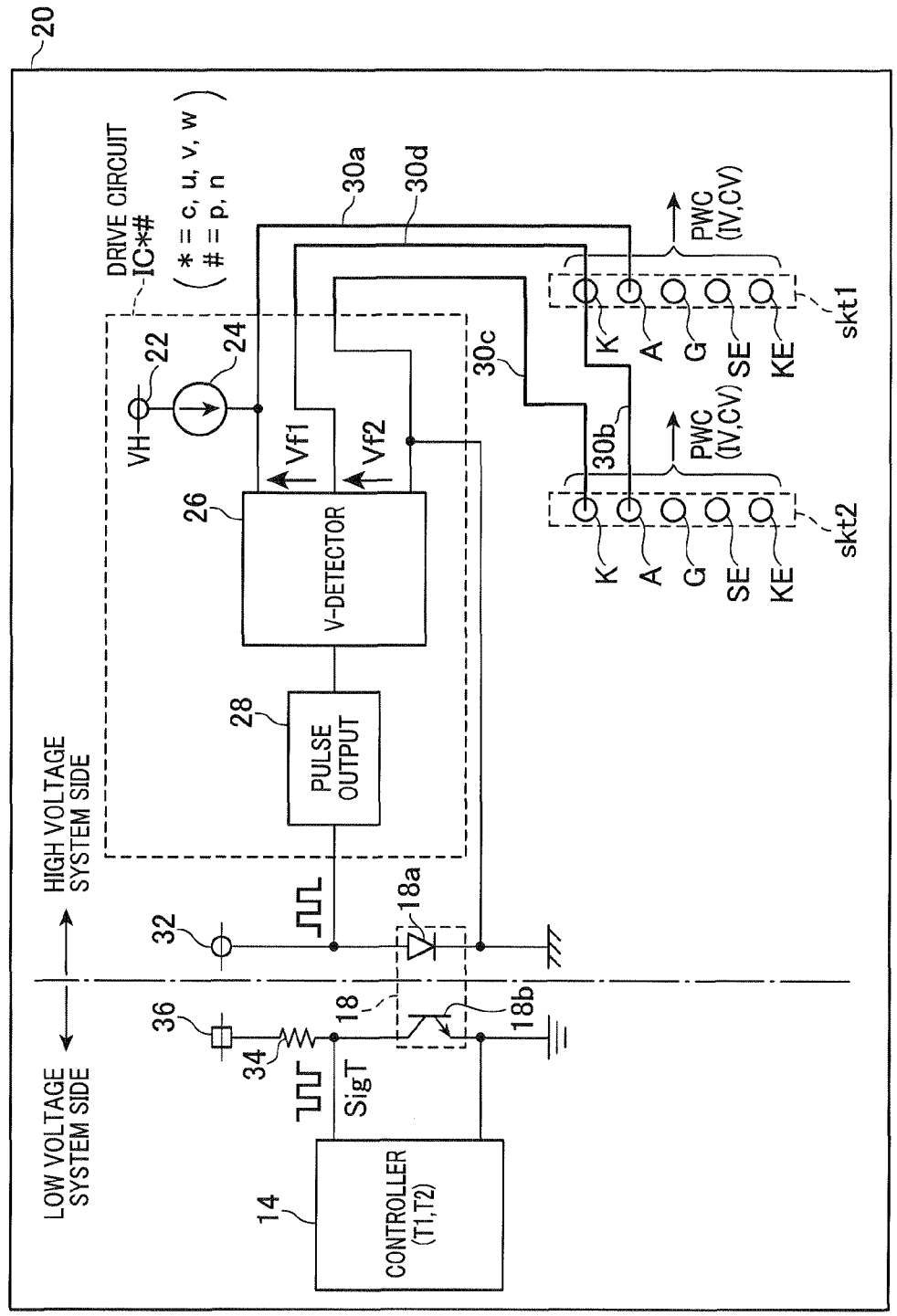
FIG. 6 is a planar view of a PCB according to a second embodiment.

FIG. 6 shows the PCB 20 according to the second embodiment. Components and the like in FIG. 6 that are the same as those in FIG. 2 are given the same reference numbers for convenience.

As shown in FIG. 6, the cathode K of the first attaching section skt1 is connected to the voltage detection circuit 26 via a wiring pattern 30d. Here, the wiring patterns 30b and 30d, the wiring pattern 30a, and the wiring pattern 30b are formed on the surface of the PCB 20 such as to be parallel with one other. In particular, the wiring patterns 30a to 30d are formed such as to be concentrated on one side of the PCB 20. This configuration is used to enhance noise resistance, as described according to the first embodiment.

The voltage detection circuit 26 detects the potential difference (referred to, hereinafter, as a first voltage difference Vf1) between both ends of the first thermo-sensitive diode T*#1 via the wiring patterns 30a and 30d. The voltage detection circuit 26 also detects the potential difference (referred to, hereinafter, as a second voltage difference Vf2) between both ends of the second thermo-sensitive diode T*#2 via the wiring patterns 30b, 30c, and 30d The first potential difference Vf1 has a negative correlation with the temperature T1 of the first switching element S*#1. The first potential difference Vf1 has a negative correlation with the temperature T1 of the first switching element S*#1. The second potential difference Vf2 has a negative correlation with the temperature T2 of the second switching element S*#2.

The pulse signal output circuit 28 outputs signals having correlation with the first potential difference Vf1 and the second potential difference Vf2. Here, according to the second embodiment, the pulse signal output circuit 28 transmits the pair of potential differences Vf1 and Vf2 to the control circuit 14 in the low voltage system by a time sharing process. As a result, the respective pieces of temperature information of the first switching element S*#1 and the second switching element S*#2 can be transmitted to the control circuit 14 by a single set of voltage detection circuit 26 and pulse signal output circuit 28.

The control circuit 14 calculates the temperature T1 of the first switching element S*#1 and the temperature T2 of the second switching element S*#2 based on the temperature detection signals SigT transmitted by the time sharing process.

According to the above-described second embodiment, the respective temperatures T1 and T2 of the first switching element S*#1 and the second switching element S*#2 can be detected. Therefore, the detection accuracy of the temperatures of the switching elements can be enhanced.

(Third Embodiment)

A third embodiment will hereinafter be described with reference to the drawings, mainly focusing on the differences with the second embodiment.

According to the third embodiment, an open failure detection process is performed to detect an open failure in the serially connected member composed of the first thermo-sensitive diode T*#1 and the second thermo-sensitive diode T*#2. When an open failure is detected, a process for short-circuiting the detected open failure area is performed.

Figure 7:
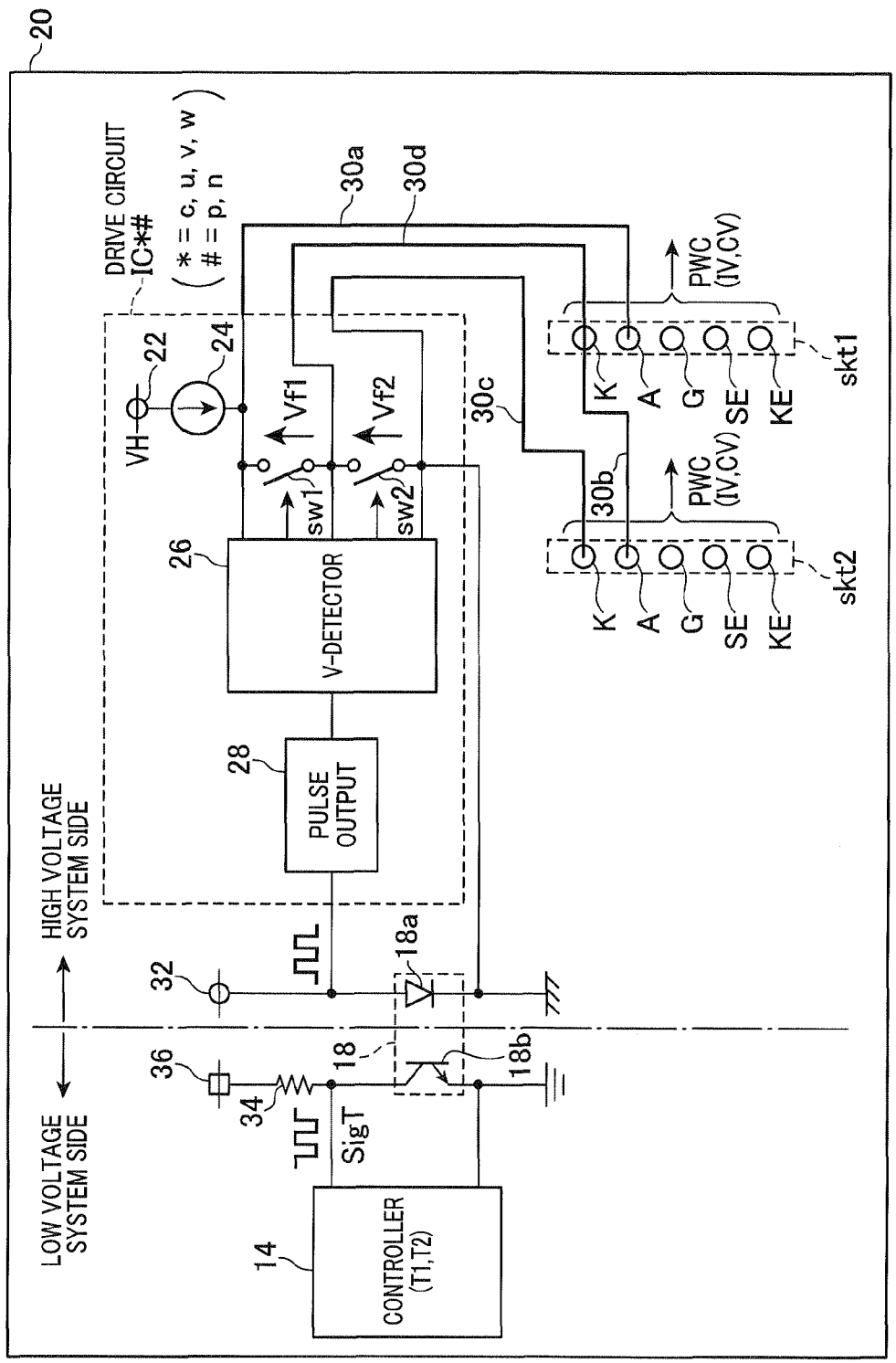
FIG. 7 is a planar view of a PCB according to a third embodiment.

FIG. 7 shows the PCB 20 according to the third embodiment. Components and the like in FIG. 7 that are the same as those in FIG. 6 are given the same reference numbers for convenience.

As shown in FIG. 7, the drive circuit IC*# includes a first switch SW1 and a second switch SW2. The first switch SW1 is opened/closed to electrically connect or disconnect the wiring pattern 30a and the wiring pattern 30d. The second switch SW2 is opened/closed to electrically connect or disconnect the wiring pattern 30d and the wiring pattern 30c. The first switch SW1 and the second switch SW2 are opened and closed by the voltage detection circuit 26. The first switch SW1 and the second switch SW2 are basically opened.

Figure 8:
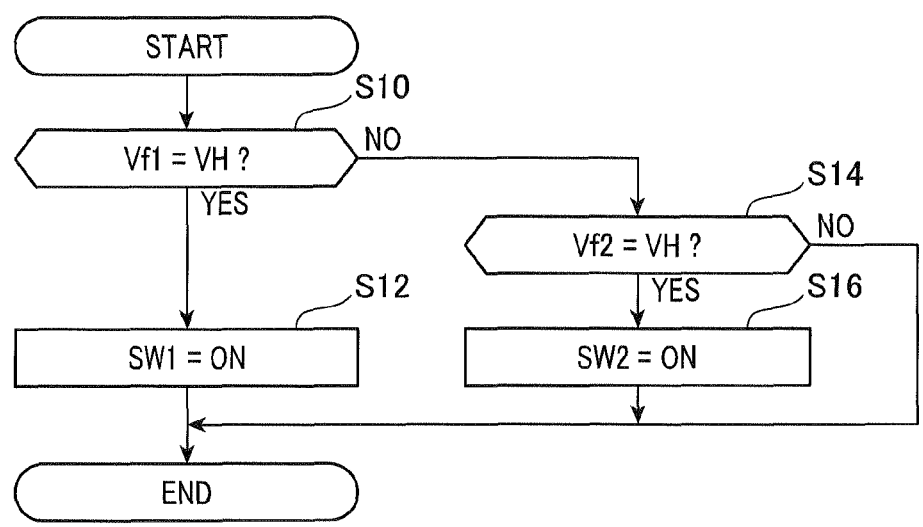
FIG. 8 is a flowchart of procedures of an open failure detection process according to the third embodiment.

Next, procedures of the open failure detection process performed by the voltage detection circuit 26 are shown in FIG. 8. The voltage detection circuit 26 according to the third embodiment is hardware. Therefore, the process in FIG. 8 is actually performed by a logic circuit.

In the series of processing operations, first, at S10, the voltage detection circuit 26 judges whether or not the first potential difference Vf1 is the same as the terminal voltage VH of the constant voltage power source 22. The voltage detection circuit 26 performs the processing operation to judge whether or not an open failure has occurred in the first thermo-sensitive diode T*#1.

When judged "YES" at S10, the voltage detection circuit 26 judges that an open failure has occurred in the first thermo-sensitive diode T*#1, and proceeds to S12. At S12, the voltage detection circuit 26 closes the first switch SW1. As a result, both ends of the first thermo-sensitive diode T*#1 in which the open failure has been detected is short-circuited.

On the other hand, when judged "NO" at S10, the voltage detection circuit 26 proceeds to S14, and judges whether or not the second potential difference Vf2 is the same as the terminal voltage VH of the constant voltage power source 22. The voltage detection circuit 26 performs the processing operation to judge whether or not an open failure has occurred in the second thermo-sensitive diode T*#2.

When judged "YES" at S14, the voltage detection circuit 26 judges that an open failure has occurred in the second thermo-sensitive diode T*#2, and proceeds to S16. At S16, the voltage detection circuit 26 closes the second switch SW2. As a result, both ends of the second thermo-sensitive diode T*#2 in which the open failure has been detected is short-circuited.

When judged "NO" at S14, or when the processing operation at S12 or S16 is completed, the series of processing operations is temporarily ended.

According to the third embodiment, when the open failure is detected, a process is performed to transmit this fact to the control circuit 14 via the interface 18.

According to the above-described third embodiment, when an open failure is detected in the serially connected member composed of the first thermo-sensitive diode T*#1 and the second thermo-sensitive diode T*#2, the open failure area is short-circuited by operation of the first switch SW1 or the second switch SW2. Therefore, detection of the temperature of the switching element can be continued for as long as possible by the thermo-sensitive diode in which the open failure has not occurred. As a result, for example, retreat running of the vehicle can be continued for as long as possible.

(Fourth Embodiment)

A fourth embodiment will hereinafter be described with reference to the drawings, mainly focusing on the differences with the second embodiment.

According to the fourth embodiment, in place of the configuration according to the first to third embodiments in which the first thermo-sensitive diode T*#1 and the second thermo-sensitive diode T*#2 are connected in series and temperature detection is performed, a configuration is used in which the thermo-sensitive diodes T*#1 and T*#2 are connected in parallel and temperature detection is performed.

Figure 9:
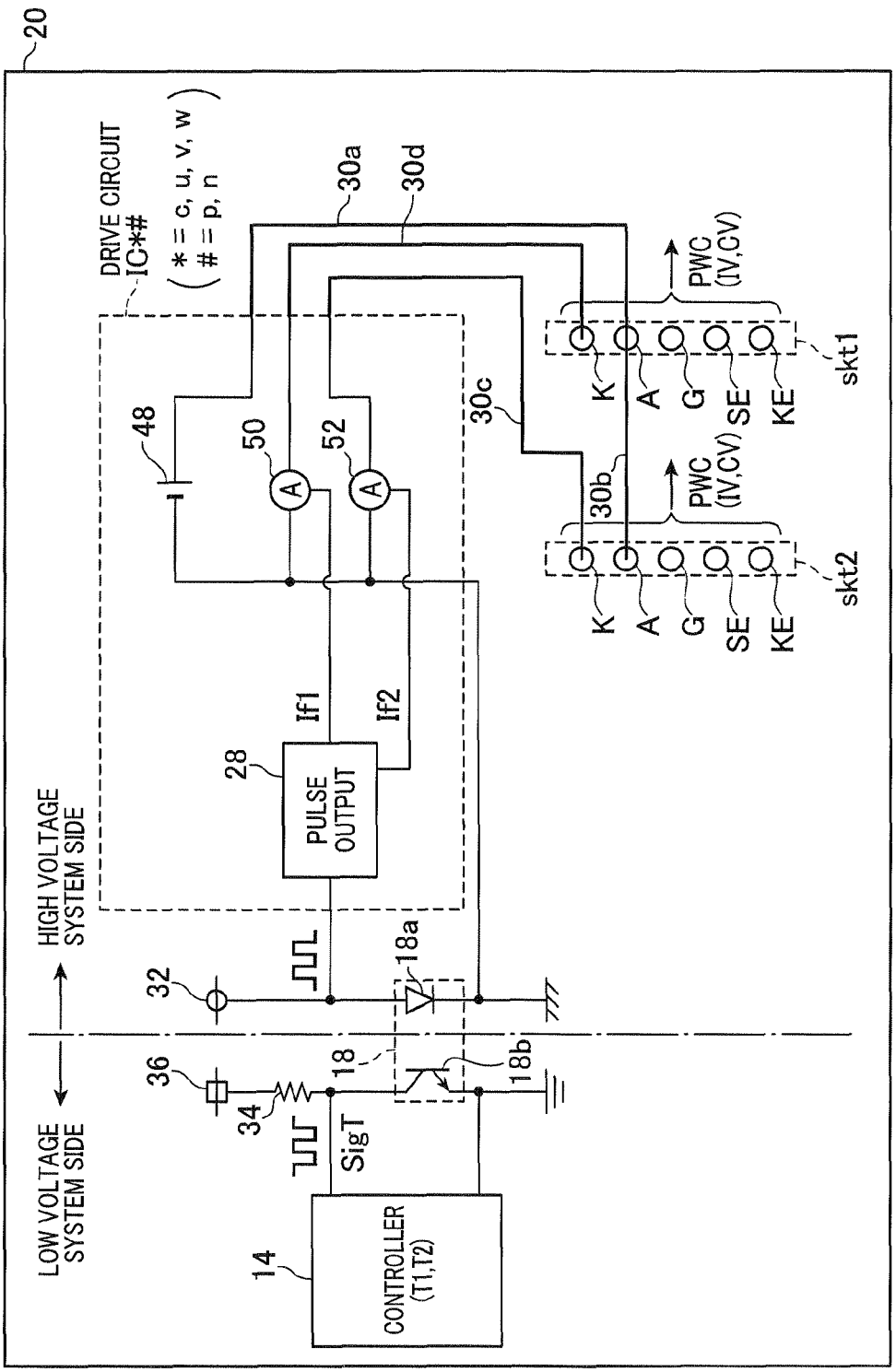
FIG. 9 is a planar view of a PCB according to a fourth embodiment.

FIG. 9 shows the PCB 20 according to the fourth embodiment. Components and the like in FIG. 9 that are the same as those in FIG. 6 are given the same reference numbers for convenience.

As shown in FIG. 9, the drive circuit IC*# includes, in addition to the above-described pulse signal output circuit 28, a power source 48, a first current detector 50, and a second current detector 52. The first current detector 50 and the second current detector 52 serve as temperature detectors. The positive electrode side of the power source 48 is connected to the anode A of the first attaching section skt1 via the wiring pattern 30a. The cathode K of the first attaching section skt1 is connected to the negative electrode side of the power source 48 via the wiring pattern 30d and the first current detector 50. The negative electrode side of the power source 48 is connected to the ground portion on the high voltage system side.

On the other hand, the anode A of the first attaching section skt1 is connected to the anode A of the second attaching section skt2 via a wiring pattern 30e. The cathode K of the second attaching section skt2 is connected to the negative electrode side of the power source 48 via the wiring pattern 30c and the second current detector 52.

According to the fourth embodiment, the respective voltage drop amounts of the first current detector 50 and the second current detector 52 are extremely small compared to the respective voltage drop amounts in the first thermo-sensitive diode T*#1 and the second thermo-sensitive diode T*#2.

In this configuration, the temperature T1 of the first switching element S*#1 and a current If1 detected by the first current detector 50 have a positive correlation. The temperature T2 of the second switching element S*#2 and a current If2 detected by the second current detector 52 have a positive correlation. The current detected by the first current detector 50 and the current detected by the second current detector 52 are both inputted into the pulse signal output circuit 28.

The pulse signal output circuit 28 transmits the respective pieces of temperature information of the first switching element S*#1 and the second switching element S*#2 to the control circuit 14 side by the above-described time sharing process, based on the signals inputted from the first current detector 50 and the second current detector 52.

As a result of the above-described configuration as well, effects other than noise resistance, among the effects described according to the first and second embodiments, can be achieved.

(Other Embodiments: Variation Examples)

The first to fourth embodiments can be modified as described below.

As the method of transmitting temperature information using the pulse signal output circuit 28 and the interface 18, for example, a method described in JP-A-2009-171312 may be used.

According to the first and second embodiments, the configuration for transmitting temperature information to the control circuit 14 via the interface 18 may be provided in correspondence with two or more pairs, among the plurality of pairs of switching elements S*#1 and S*#2 included in the converter CV and the inverter IV.

The first region and the second region are not limited to those given as examples according to the first embodiment. For example, should a temperature detection value of some sort in the low voltage system be required to be transmitted from the low voltage system side to the high voltage system side, the low voltage system can be first region and the high voltage system can be the second region.

According to the fourth embodiment, a configuration may be used in which the first current detector 50 and the second current detector 52 are eliminated, and a single current detector is provided in the direct vicinity of the negative electrode side of the power source 48. In this instance, the current detector can detect the average temperature Tave of the first switching element S*#1 and the second switching element S*#2.

The temperature detecting element is not limited to the thermo-sensitive diode and may be, for example, a resistor (temperature measurement resistor). In this instance, as a specific configuration for temperature detection, for example, a configuration may be used in which, instead of the thermo-sensitive diodes, a plurality of resistors are connected in series. A current is supplied to the serially connected member by a constant current power source (see FIG. 2). Even in an instance in which this configuration is used, the average temperature Tave of the first switching element S*#1 and the second switching element S*#2 can be detected based on a potential difference V1 between both ends of the serially connected member composed of the temperature measurement resistors. Here, the higher the temperature of the switching element is, the greater the voltage drop amounts of the resistors. Therefore, the higher the average temperature Tave is, the greater the potential difference V1 tends to be.

In addition, as a specific configuration for temperature detection in an instance in which the resistors are used, for example, a configuration may be used in which, instead of the thermo-sensitive diodes, the plurality of resistors are connected in parallel. A voltage is applied to the parallel-connected member by a common constant voltage power source (see FIG. 9).

The interface 18 is not limited to that including an opto-insulating element and may, for example, include a magnetically insulating element (such as a pulse transformer).

The plurality of temperature detection objects are not limited to those given as an example according to the first embodiment. For example, a parallel-connected member composed of at least two or more switching elements S*n¥, among the switching elements S*n¥ on the low potential side, may be the temperature detection object.

The switching element to be the temperature detection object is not limited to the IGBT and may be, for example, a metal-oxide-semiconductor field-effect transistor (MOSFET).

The temperature detection object is not limited to the pair of switching elements S*#1 and S*#2 connected to each other in parallel. For example, the temperature detection object may be three or more switching elements connected to each other in parallel. Here, for example, when the temperature detection object is the lo parallel-connected member composed of three switching elements, a configuration may be used in which the average temperature Tave is detected for a pair of switching elements, among the switching elements, and an individual temperature is detected for the remaining switching element. A configuration such as this may be used when, for example, the temperature detection accuracy required for one of the switching elements is higher than that for the other switching elements.

In addition, the temperature detection object is not limited to a plurality of switching elements connected to each other in parallel, and may be a single switching element. In this instance, the plurality of temperature detection object may be, for example, at least two of the switching elements S*n¥ on the low potential side, as described above.

Furthermore, the temperature detection object is not limited to the switching elements S*#¥ included in the inverter IV and the converter CV, and is not limited to that included in power conversion circuits, such as the inverter IV and the converter CV.

What is claimed is:

1. A temperature detecting device that is applied to a power conversion circuit comprising a plurality of series connections of a set of switching elements on a high potential side which are connected in parallel to each other and a set of switching elements on a low potential side which are connected in parallel to each other, the plurality of series connections being connected in parallel to each other, the temperature detecting device comprising:
a plurality of temperature detecting elements that are disposed so as to correspond to each of the switching elements configuring the power conversion circuit and, by supplied electric power, output a signal having a correlation with a temperature of each of the switching elements;
a temperature detector that is disposed for each of the sets and detects a temperature of each of the switching elements configuring each of the sets, based on output signals from each of the temperature detecting elements corresponding to each of the switching elements configuring each of the sets; and
a common power source that is disposed for each of the sets and supplies electric power to each of the temperature detecting elements corresponding to each of the switching elements configuring each of the sets,
wherein:
the temperature detecting elements corresponding to each of the switching elements configuring each of the sets are connected in series or in parallel to each other; and
the temperature detector detects an average temperature of at least two switching elements among the plurality of switching elements which are connected in parallel to each other, or respective temperatures of the plurality of switching elements which are connected in parallel to each other, based on the output signals.

2. The temperature detecting device according to claim 1, wherein:
each of the switching elements configuring each of the sets is turned ON and OFF by a common operating signal;
the temperature detecting elements corresponding to each of the switching elements configuring each of the sets are connected in series to each other;
the power source is a constant current power source connected to one end of series connection of the temperature detecting elements corresponding to each of the switching elements configuring each of the sets; and
the temperature detector detects an average temperature of the plurality of switching elements which are connected in parallel to each other, based on a potential difference between both ends of series connection of the temperature detecting elements.

3. The temperature detecting device according to claim 1, wherein:

the temperature detecting elements corresponding to each of the switching elements configuring each of the sets are connected in series to each other;
the power source is a constant current power source connected to one end of series connection of the temperature detecting elements corresponding to each of the switching elements configuring each of the sets; and
the temperature detector detects respective temperatures of the plurality of switching elements which are connected in parallel to each other, based on a potential difference between both ends of each of the temperature detecting elements.

4. The temperature detecting device according to claim 2, wherein:
the plurality of temperature detecting elements and the temperature detector are disposed on a circuit board;
the temperature detector and at least each of both ends of series connection of the temperature detecting elements are formed on the circuit board and are connected to each other via a plurality of wiring patterns for detecting output signals of the temperature detecting elements; and
the plurality of wiring patterns are mutually being formed in parallel to each other on the circuit board in a front view of a plate surface of the circuit board.

5. The temperature detecting device according to claim 3, wherein:
the plurality of temperature detecting elements and the temperature detector are disposed on a circuit board;
the temperature detector and at least each of both ends of series connection of the temperature detecting elements are formed on the circuit board and are connected to each other via a plurality of wiring patterns for detecting output signals of the temperature detecting elements; and
the plurality of wiring patterns are mutually being formed in parallel to each other on the circuit board in a front view of a plate surface of the circuit board.

6. The temperature detecting device according to claim 2, further comprising:
a failure detector that detects an open failure in the series connection of temperature detecting elements corresponding to each of the switching elements configuring each of the sets; and
short-circuiting means for short-circuiting a detected area of the open failure, based on the open failure detected by the failure detector.

7. The temperature detecting device according to claim 3, further comprising:
a failure detector that detects an open failure in the series connection of temperature detecting elements corresponding to each of the switching elements configuring each of the sets; and
short-circuiting means for short-circuiting a detected area of the open failure, based on the open failure detected by the failure detector.

8. The temperature detecting device according to claim 4, further comprising:
a failure detector that detects an open failure in the series connection of temperature detecting elements corresponding to each of the switching elements configuring each of the sets; and
short-circuiting means for short-circuiting a detected area of the open failure, based on the open failure detected by the failure detector.

9. The temperature detecting device according to claim 5, further comprising:

a failure detector that detects an open failure in the series connection of temperature detecting elements corresponding to each of the switching elements configuring each of the sets; and short-circuiting means for short-circuiting a detected area of the open failure, based on the open failure detected by the failure detector.

10. The temperature detecting device according to claim 1, wherein the temperature detecting elements are thermo-sensitive diodes.

11. The temperature detecting device according to claim 2, wherein the temperature detecting elements are thermo-sensitive diodes.

12. The temperature detecting device according to claim 3, wherein the temperature detecting elements are thermo-sensitive diodes.

13. The temperature detecting device according to claim 4, wherein the temperature detecting elements are thermo-sensitive diodes.

14. The temperature detecting device according to claim 5, wherein the temperature detecting elements are thermo-sensitive diodes.

15. The temperature detecting device according to claim 1, further comprising:

transmitting means that transmits information related to the temperature detected by the temperature detector to a second region that is electrically insulated from a first region in which the switching elements, the temperature detecting elements, and the temperature detector are disposed.

16. The temperature detecting device according to claim 2, further comprising:

transmitting means that transmits information related to the temperature detected by the temperature detector to a second region that is electrically insulated from a first region in which the switching elements, the temperature detecting elements, and the temperature detector are disposed.

17. The temperature detecting device according to claim 3, further comprising:

transmitting means that transmits information related to the temperature detected by the temperature detector to a second region that is electrically insulated from a first region in which the switching elements, the temperature detecting elements, and the temperature detector are disposed.

18. The temperature detecting device according to claim 4, further comprising:

transmitting means that transmits information related to the temperature detected by the temperature detector to a second region that is electrically insulated from a first region in which the switching elements, the temperature detecting elements, and the temperature detector are disposed.

19. The temperature detecting device according to claim 5, further comprising:

transmitting means that transmits information related to the temperature detected by the temperature detector to a second region that is electrically insulated from a first region in which the switching elements, the temperature detecting elements, and the temperature detector are disposed.

* * * * *